(12) United States Patent
Abboud et al.

(10) Patent No.: US 6,440,126 B1
(45) Date of Patent: Aug. 27, 2002

(54) CRYOBLATION CATHETER HANDLE

(75) Inventors: Marwan Abboud, Pierrefonds; Domenic Santoianni, Kirkland; Philippe Marchand, Hudson, all of (CA)

(73) Assignee: CryoCath Technologies, Kirkland (CA)

( * ) Notice: Subject to any disclaimer, the term of this patent is extended or adjusted under 35 U.S.C. 154(b) by 0 days.

(21) Appl. No.: 09/556,042

(22) Filed: Apr. 21, 2000

Related U.S. Application Data

(60) Provisional application No. 60/130,538, filed on Apr. 21, 1999.

(51) Int. Cl.$^7$ .............................................. A61B 18/18
(52) U.S. Cl. ............................................ 606/22; 606/21
(58) Field of Search ...................... 606/20–26; 604/35, 604/264, 523, 535; 600/136

(56) References Cited

U.S. PATENT DOCUMENTS

| | | | |
|---|---|---|---|
| 4,043,341 A | | 8/1977 | Tromovitch .............. 128/303.1 |
| 4,534,339 A | * | 8/1985 | Collins et al. .............. 600/105 |
| 4,919,112 A | * | 4/1990 | Siegmund .................. 600/105 |
| 4,946,440 A | | 8/1990 | Hall ............................ 604/95 |
| 5,078,713 A | | 1/1992 | Varney ........................ 606/23 |
| 5,098,428 A | | 3/1992 | Sandlin et al. ................ 606/22 |
| 5,170,787 A | | 12/1992 | Lindegren .................. 128/642 |
| 5,217,482 A | | 6/1993 | Keith ......................... 606/194 |
| 5,324,286 A | | 6/1994 | Fowle ......................... 606/23 |
| 5,334,181 A | | 8/1994 | Rubinsky et al. ............. 606/22 |
| 5,423,807 A | * | 6/1995 | Milder ......................... 606/20 |
| 5,452,582 A | | 9/1995 | Longsworth ................. 62/51.2 |
| 5,658,278 A | | 8/1997 | Imran et al. .................. 606/41 |
| 5,674,218 A | | 10/1997 | Rubinsky et al. ............. 606/20 |
| 5,685,878 A | | 11/1997 | Falwell et al. ................ 606/49 |
| 5,697,927 A | | 12/1997 | Imran et al. .................. 606/41 |
| 5,715,817 A | | 2/1998 | Stevens-Wright et al. .. 128/642 |
| 5,860,953 A | * | 1/1999 | Snoke et al. .................. 604/95 |
| 5,860,970 A | | 1/1999 | Goddard et al. ............... 606/23 |
| 5,916,212 A | * | 6/1999 | Baust et al. .................. 606/22 |
| 6,007,571 A | * | 12/1999 | Neilson et al. ................ 606/22 |
| 6,221,070 B1 | * | 4/2001 | Tu et al. ..................... 600/146 |
| 6,224,624 B1 | * | 5/2001 | Lashevas et al. ............. 606/20 |

* cited by examiner

Primary Examiner—Linda C. M. Dvorak
Assistant Examiner—David M. Ruddy
(74) Attorney, Agent, or Firm—Christopher & Weisberg, P.A.

(57) ABSTRACT

A cryocatheter system includes a first handle portion having a proximal end, a distal end, a first fluid flow path, and a second fluid flow path; a second handle portion having a proximal end, a distal end, a first fluid flow path, and a second fluid flow path; and a catheter having a proximal end, a distal end, a first fluid flow path, and a second fluid flow path. The distal end of the first handle portion is matable with the proximal end of the second handle portion to place the respective first and second fluid flow paths of each handle portion in fluid communication; and the distal end of the second handle portion is matable with the proximal end of the catheter to place the respective first and second fluid flow paths of the second handle portion and the catheter in fluid communication.

20 Claims, 6 Drawing Sheets

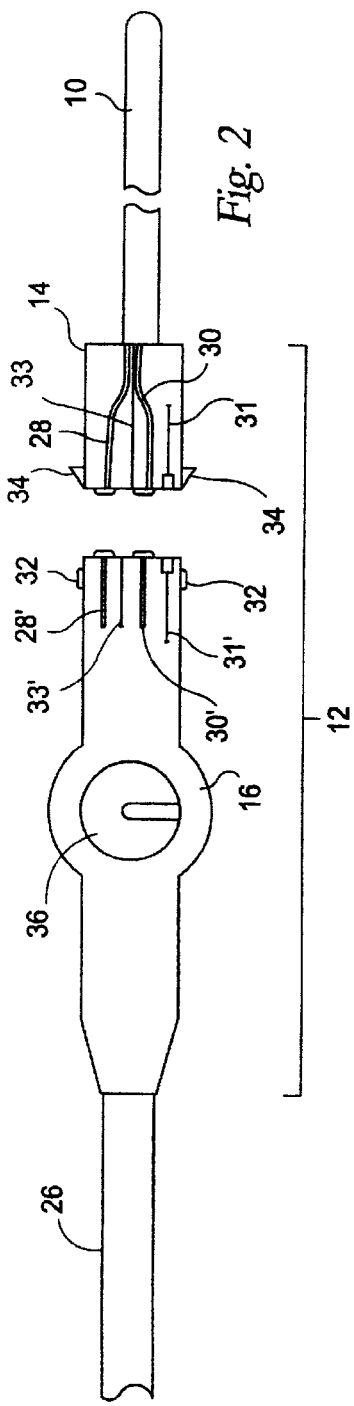
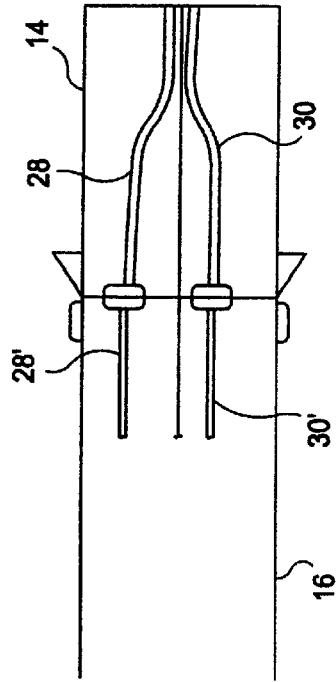
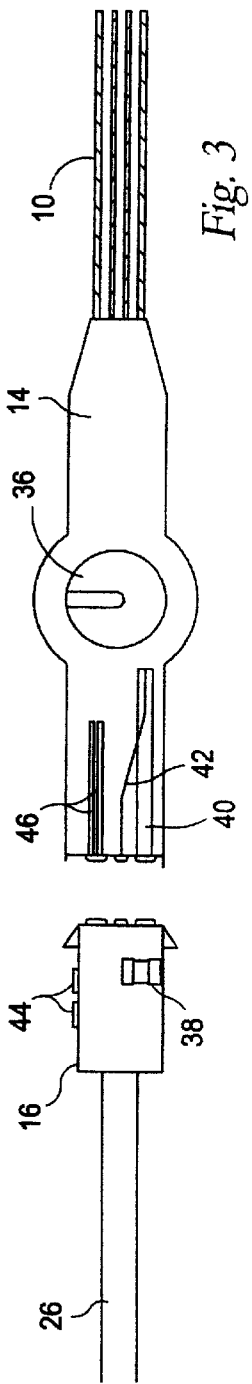
Fig. 2
Fig. 2A
Fig. 3

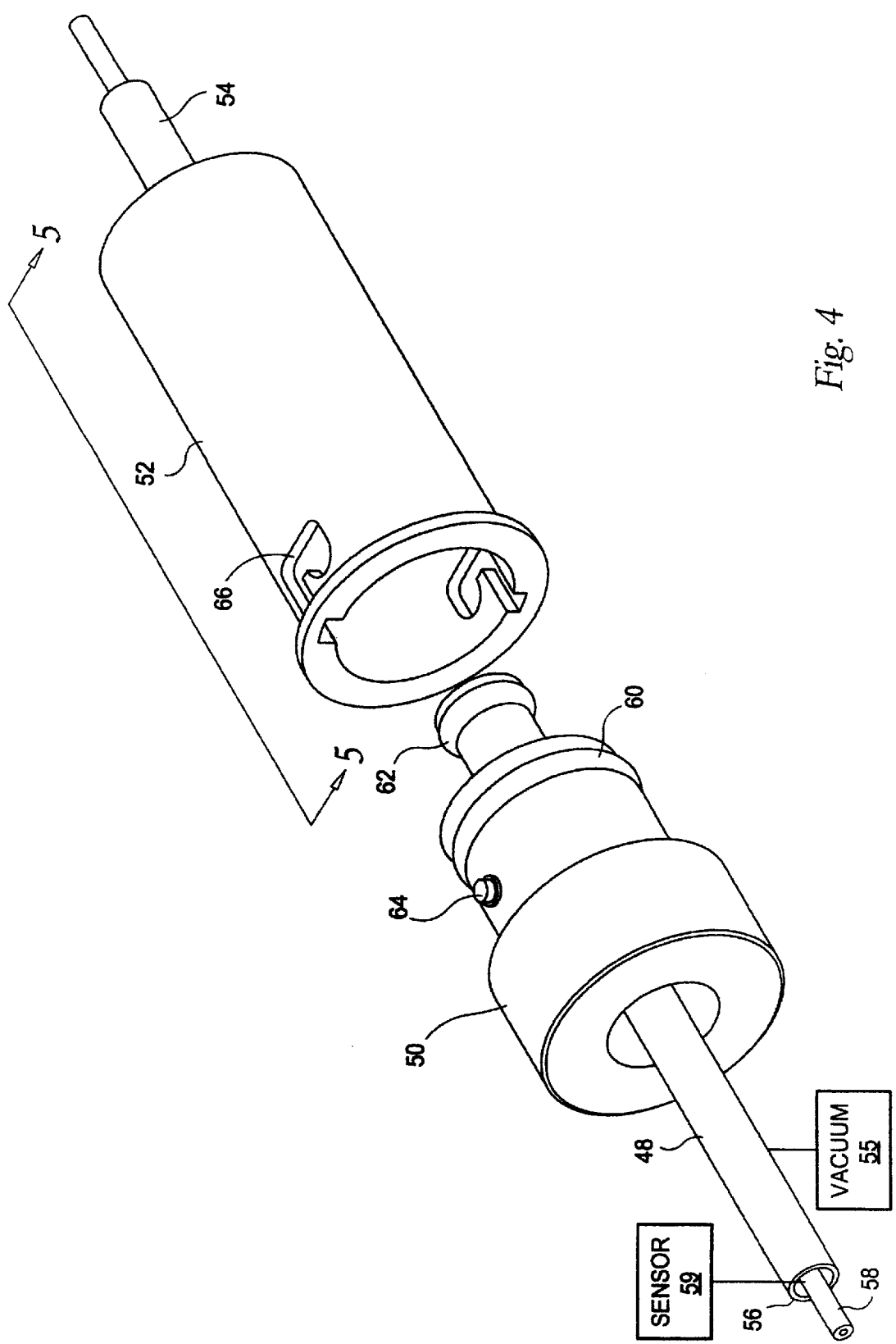

CRYOBLATION CATHETER HANDLE

CROSS-REFERENCE TO RELATED APPLICATIONS

This application claims priority from U.S. Provisional Patent Application Ser. No. 60/130,538, filed Apr. 21, 1999.

STATEMENT REGARDING FEDERALLY SPONSORED RESEARCH

Not applicable.

FIELD OF THE INVENTION

This invention relates to catheters, and more particularly to handles and connectors for cryogenic catheters.

BACKGROUND OF THE INVENTION

A cryocatheter can generally be described as an elongate, slender, flexible body that is capable of delivering extreme cold to provide a medically therapeutic effect. Such a catheter can be a part of a system that includes several components, such as a console, an umbilical, a cryoblation catheter and a handle.

The console houses the electronics and software for controlling an ablation procedure. Additionally, the console controls delivery of a refrigerant through the umbilical to the catheter and recovery of the refrigerant from the catheter.

The umbilical connecting the catheter and handle to the console provides mechanical connections for refrigerant transport and electrical connection for electrical devices and sensors. The handle, in addition to providing an appropriate graspable structure, can include controls for catheter steering, as well as other catheter functions.

Known cryocatheter systems provide a unitary handle and catheter which is intended for a single use. As with other devices, attention to the percentage and content of a system that is disposable (or that which must be disposed of for sanitary reasons), as well as attention to the cost of replacement items, can have a substantial effect on the cost of acquisition and operation of the system. Thus, if possible, it would help to reduce cost of the system if only the catheter (or a portion thereof) were disposable and, under most circumstances, the handle were available for reuse.

Ideally, the inclusion of disposable system elements does not compromise system performance or patient safety. However, known attempts to provide disposable catheter elements have been less than ideal. For example, providing a catheter that is removable from the handle requires not only connection to refrigerant, steering elements and electrical elements, but also a creation of a fluid-tight seal at the catheter/handle interface. Not only can it be tedious to make such connections, known devices with this type of feature have not proved to be acceptable with respect to either performance or safety. It would therefore be desirable to provide a cryocatheter and handle that provides the benefits of a disposable component and which is easy to use, without safety or performance limitations.

SUMMARY OF THE INVENTION

The present invention provides a cyrocatheter system having a two-part handle that is easy to connect and use; but the system does not compromise safety and performance requirements.

In an exemplary embodiment, a cryocatheter system includes a first handle portion having a proximal end, a distal end, a first fluid flow path, and a second fluid flow path; a second handle portion having a proximal end, a distal end, a first fluid flow path, and a second fluid flow path; and a catheter having a proximal end, a distal end, a first fluid flow path, and a second fluid flow path. The distal end of the first handle portion is matable with the proximal end of the second handle portion to place the respective first and second fluid flow paths of each handle portion in fluid communication; and the distal end of the second handle portion is matable with the proximal end of the catheter to place the respective first and second fluid flow paths of the second handle portion and the catheter in fluid communication.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 2 illustrates an exemplary embodiment of a handle as shown in FIG. 1, wherein the two handle portions are not mated;

FIG. 2A depicts the first and second handle portions of FIG. 2 in a mated state;

FIG. 3 shows an alternative embodiment of a two-part handle;

FIG. 4 is an exploded view of a two-part co-axial handle;

DETAILED DESCRIPTION OF THE INVENTION

Figure 1:
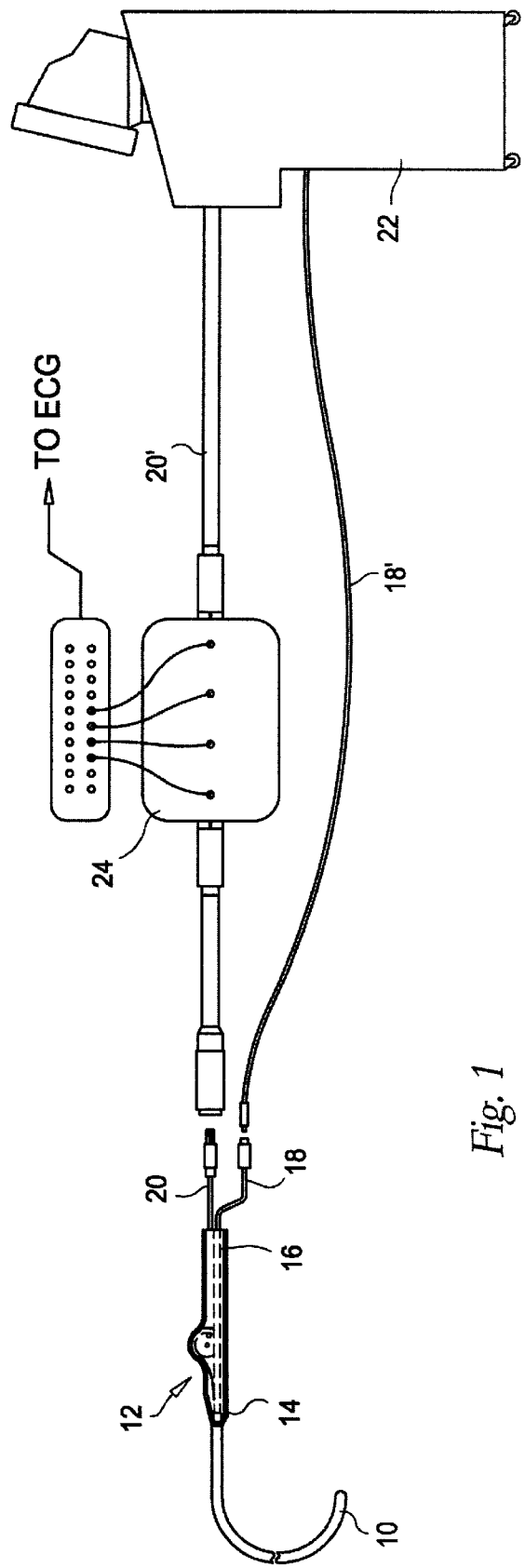
FIG. 1 illustrates a cryocatheter system generally.

FIG. 1 depicts a cryocatheter system in accordance with the invention. The system includes a catheter 10, such as those disclosed in U.S. Pat. Nos. 5,899,898 and 5,899,899 to Arless, which are incorporated herein by reference. The system also includes a handle 12 having a first portion 14 and a second portion 16. First and second umbilicals 18 and 20, respectively, connect the second portion 16 of the handle 12 to a console 22. The first umbilical 18 provides a path for a liquid or gas refrigerant to be transferred between the console 22 and the handle 12; and the second umbilical 20 provides a signal path, such as for electrical signals, between the console 22 and the handle. Additional umbilicals can be provided as required, and the functions of more than one umbilical can be provided in a single, multifunction umbilical. Further, additional devices, such as a connector box 24 can be placed in electrical communication with an umbilical. As shown in FIG. 1, the connector box 24 provides for connection to ECG apparatus (not shown). Also, one or more of the umbilicals can be divisible into two or more portions as shown in FIG. 1, wherein the first umbilical includes portion 18 and 18', and the second umbilical includes portions 20 and 20'.

Referring now to FIG. 2, additional details of an exemplary two-part handle 12 are discussed in greater detail. A first handle portion 14 is shown mated to a cryocatheter 10 and a second handle portion 16 is shown mated to a single, multipurpose umbilical 26. The first handle portion 14 defines or includes a portion of a first fluid pathway 28 and a portion of a second fluid pathway 30. The second handle portion 16 defines or contains a second portion of the first fluid pathway 28' and a second portion of the second fluid pathway 30'. When the first and second portions of the first and second fluid pathways are mated, as shown in FIG. 2A, continuous fluid paths are provided. Similarly, the first handle portion 14 includes a portion of one or more electrical or fiber-optic lines 31 and the second handle portion 16 includes a second portion of the one or more electrical or fiber-optic lines 31'. Further, the first handle portion 14 includes a portion of one or more steering elements, such a pull wire 33 and the second handle portion 16 includes a second portion of the steering elements 33'.

The first and second handle portions, as well as the first and second fluid pathways, one or more electrical or fiber-optic lines, and one or more steering elements are held together by complimentary locking elements 32 and 34 as is known in the art, such as locking clips, bayonet, or twist-lock. Similarly, the fluid paths are mated with couplings, the wires with electrical connectors, and the steering elements with mechanical connectors. Thus, in the exemplary embodiment, the catheter 10 can be disconnected from the umbilical 14 and discarded, while allowing the first handle portion 18, which can include steering mechanisms and other controls, to be retained for further use.

Whereas FIG. 2 shows a steering actuator, such as a thumb wheel, for selectively positioning a steering element in the second portion 16 of the handle 12, FIG. 3 shows an arrangement where the steering actuator 36 is located in the first portion 14. Additional features visible in FIG. 3 include a blood sensor 38 located and configured in such a manner so as to detect blood being withdrawn from the catheter 10 through a low pressure or vacuum exhaust line 40 along with refrigerant injected through a supply tube 42. Also shown are electrical controls 44 in communication with electrical wires 46.

In addition to the above features, the refrigerant injection and low pressure or vacuum return lines can be configured coaxially either in an umbilical or in the handle as shown in FIG. 4. In this illustration an umbilical 48, a first connector 50 or handle portion, a second connector 52 or handle portion, and second umbilical 54 or catheter are shown. The umbilical 48 includes an outer tube 56 and an inner tube 58. In the exemplary embodiment, the inner tube 58 provides a path for fluid (e.g., refrigerant) under positive pressure, whereas the outer tube 56 provides a path for fluid under reduced or low pressure (e.g., in connection to a vacuum pump 55). Thus, if a leak should occur at some point along the inner tube 58 or its connections to other components, the low pressure environment allows the leak to be contained, thereby preventing refrigerant from escaping the umbilical 48. Additional safety is provided by a sensor 59 in communication with the low-pressure fluid path defined by the outer tube 56. The sensor 59 is tuned to detect a change in pressure within the outer tube 56, and when a change is detected, fluid flow into the system is turned off, as a change in pressure can be an indicator that a leak is present in the system.

Continuing to refer to FIG. 4, the umbilical 48 is mated to the first connector 50 and the umbilical 54 is mated to the second connector 52. The first connector 50 includes O-rings 60 and 62 and is matable with the second connecter 52, as shown in greater detail in the figures that follow, to provide a fluid-tight connection. The first connector 50 can be locked to the second connector 52 with the assistance of a bayonet-type connection having complimentary protuberances 64 and engagement slots 66.

Figure 5:
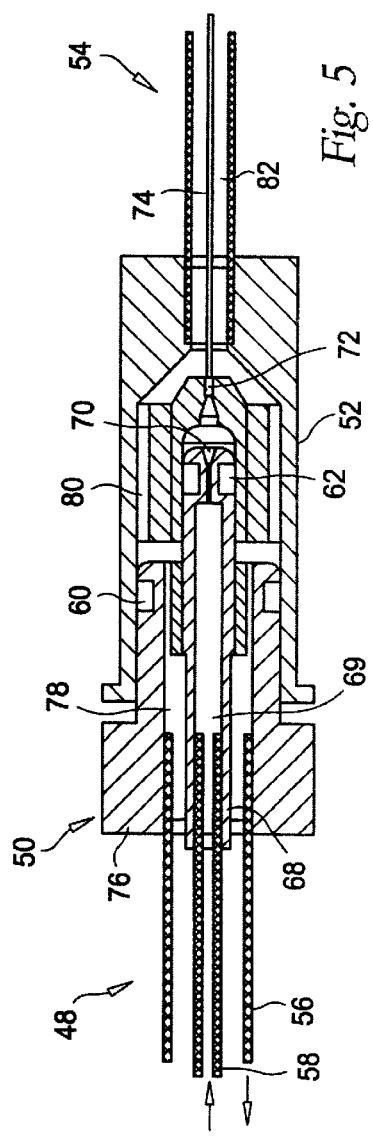
FIG. 5 is a sectional view of the two-part co-axial handle of FIG. 4 in a partially mated state.

FIG. 5 is a cross-sectional view of the coaxial connector of FIG. 4 along line 5—5. In this view, the first connector 50 is shown almost fully mated to the second connector 52. In this view the inner tube 58 is shown mated to an inner portion 68 of the first connector 50. The inner portion 68 defines a fluid path 69 leading to an outlet 70 that, when the first and second connectors 50 and 52 are mated, aligns with a fluid inlet 72 to an injection tube 74. The O-ring 62 ensures good sealing of the connection.

Similarly, the outer tube 56 is shown mated to an outer portion 76 of the first connector 50. The outer portion defines a fluid path 78 that is in fluid communication with a fluid path 80 defined by the second connector 52. The fluid path 80 leads to, and is in communication with a fluid path 82 in the umbilical 54. The O-ring 60 ensures a good seal between the first and second connectors 50 and 52, respectively.

Figure 6:
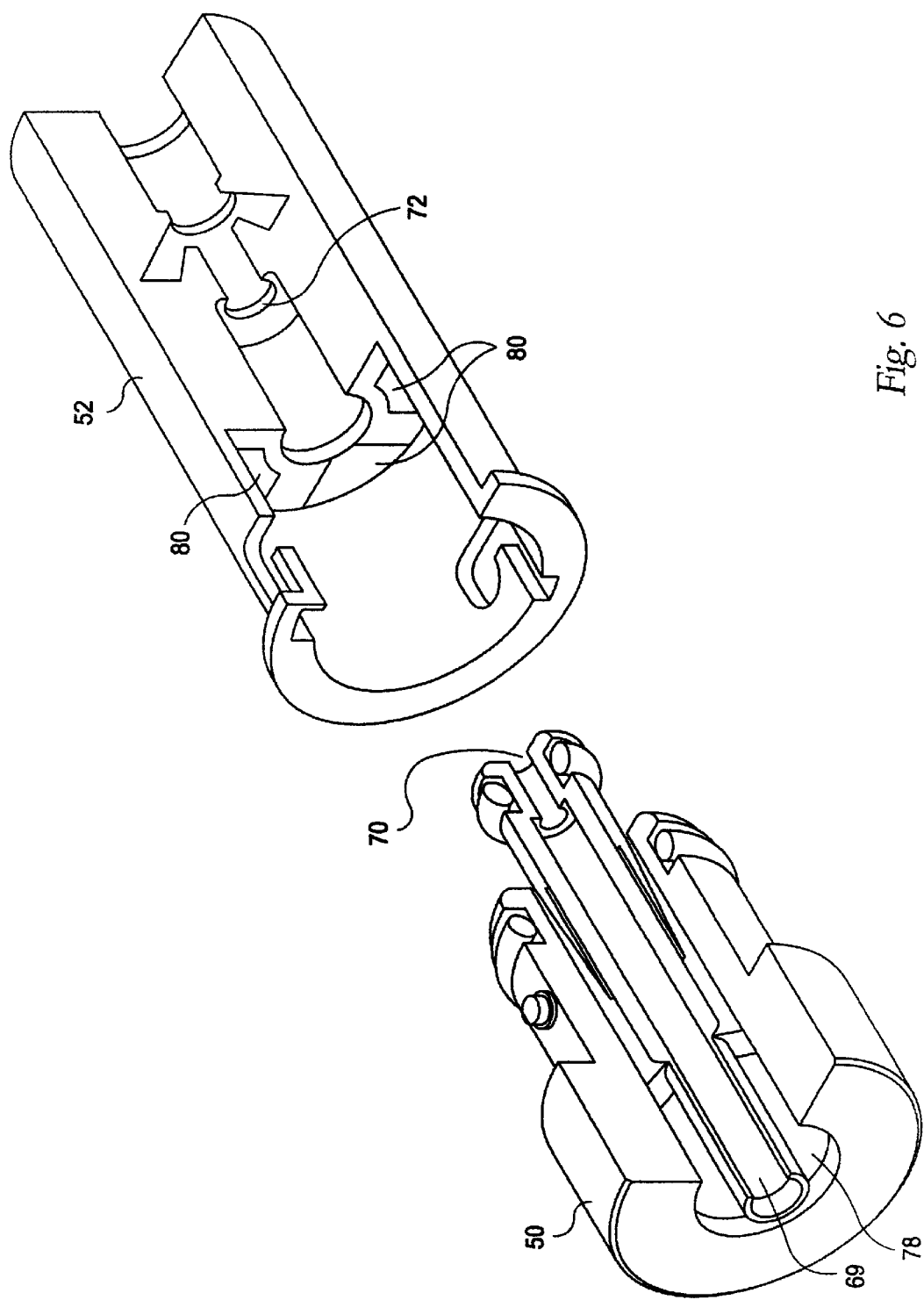
FIG. 6 illustrates additional features of the handle of FIG. 4 in an exploded cutaway view.

FIG. 6 is a cut-away view of the assembly shown in FIG. 6. In this view, the fluid path 69, outlet 70, fluid inlet 72, fluid path 78, fluid path 80 are all clearly visible.

Figure 7:
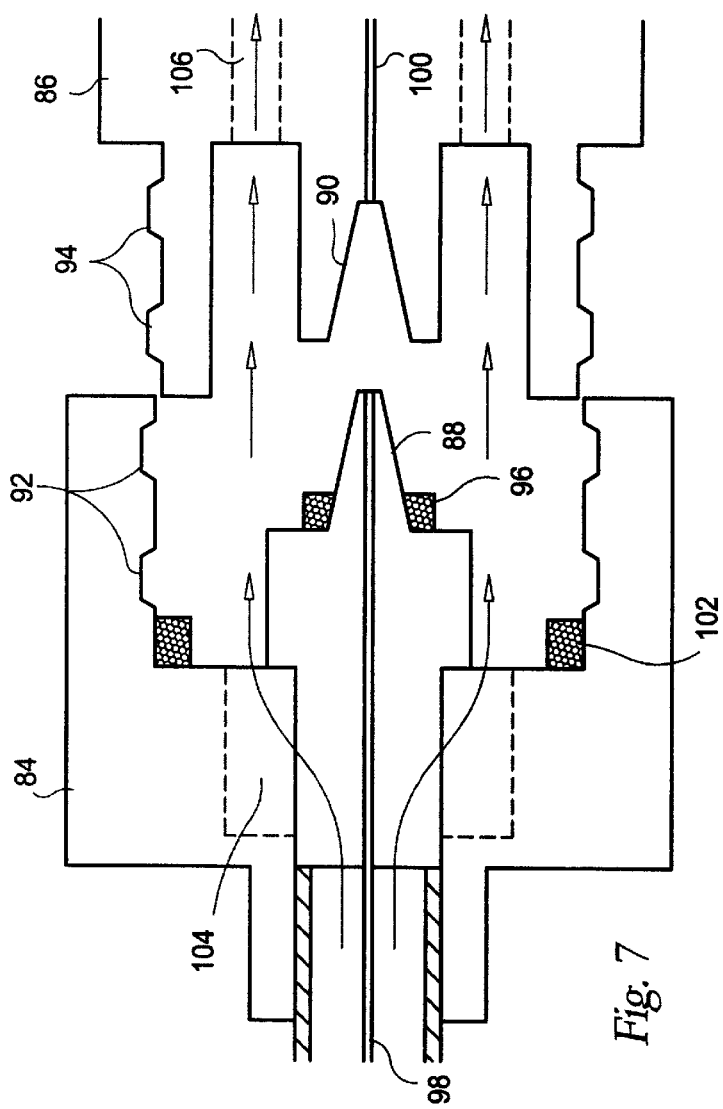
FIG. 7 is a sectional view of another embodiment of a co-axial connection.

FIG. 7 shows an alternative embodiment of a coaxial arrangement. Shown is a first connector 84 and a second connector 86. In this embodiment, a male Leur taper fitting 88 is receivable within a female Leur taper receptacle 90 as complimentary locking threads 92 and 94 on the first and second connectors are engaged. When the connectors are fully engaged an O-ring seal 96 prevents leakage for connecting fluid flow paths 98 and 100. Similarly, an o-ring seal 102 prevents leakage for connecting fluid flow paths 104 and 106. Exemplary fluid flow through flow paths 104 and 106 is shown by arrows.

Figure 8:
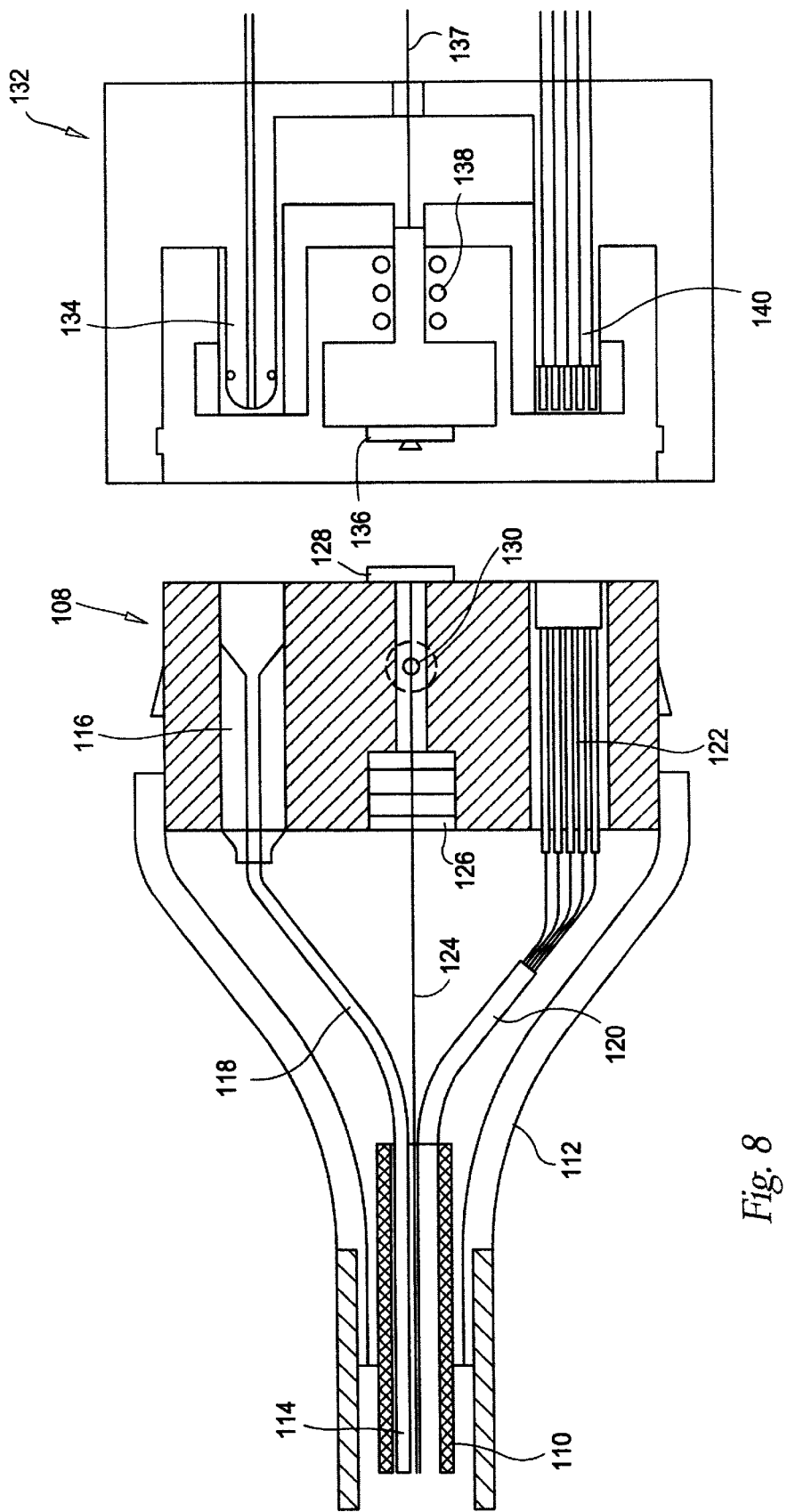
FIG. 8 is yet another embodiment of a co-axial connection.

Yet another connector embodiment is shown in FIG. 8. This embodiment provides connections that are not coaxial. As shown, a first connector 108 is mated to an outer tube or catheter shaft 110 with a rigid sleeve 112 and a flexible strain relief element. An fluid injection tube 114 is connected to a high-pressure female connector fitting 116 with a flexible connector tube 118. Electrical wires 120 that pass through the outer tube 110 terminate at a female pin wire connector 122. A pull-wire 124 passes through the outer tube 110 and a pull-wire seal fitting 126 to a female pull-wire connector 128. A pull-wire tension adjuster 130 can also be provided.

A second connector 132 includes a male, high-pressure. connector 134 that is matable with the fitting 116 to provide a continuous fluid path. A male pull-wire connector 136, matable with the connector 128, is axially movable within a portion of the second connector 132 as shown by the double-headed arrow. The connector 136 is secured to a pull-wire 137 that is in turn secured to an actuator (such as element 36 shown in FIGS. 2 and 3). Thus, when the pull-wire 137 is moved axially, the connector 136 moves axially. A bias force can be applied by a bias element 138, such as a spring, to push the connector 136 to a selected point when axial tension is reduced on the pull-wire. Also shown is a male wire pin connector 140.

A variety of modifications and variations of the present invention are possible in light of the above disclosure. It is therefore understood that, within the scope of the appended claims, the present invention may be practiced otherwise than as specifically described hereinabove.

What is claimed is:

1. A cryocatheter system comprising:
   a first handle portion having a proximal end, a distal end, a first fluid flow path, and a second fluid flow path;

a second handle portion having a proximal end, a distal end, a first fluid flow path, and a second fluid flow path, wherein the distal end of the first handle portion is matable with the proximal end of the second handle potion to place the respective first and second fluid flow paths of each handle portion in fluid communication; and a flexible catheter having a proximal end, a distal end, a first fluid flow path, and a second fluid flow path, wherein the distal end of the second handle portion is matable with the proximal end of the catheter to place the respective first and second fluid flow paths of the second handle portion and the catheter in fluid communication.

2. The cryocatheter of claim 1, further comprising a pressure sensor in communication with one of the first and second fluid flow paths.

3. The cryocatheter of claim 1, further comprising a blood detector in communication with one of the first and second fluid flow paths.

4. The cryocatheter of claim 1, wherein the first fluid flow path is coaxial with second fluid flow path.

5. The cryocatheter of claim 4, wherein the first fluid flow path is defined by a refrigerant supply tube and the second fluid flow path is defined by a fluid exhaust tube.

6. The cryocatheter of claim 5, wherein the refrigerant supply tube is disposed within the fluid exhaust tube.

7. The cryocatheter of claim 5, wherein the fluid exhaust tube is in fluid communication with a vacuum source.

8. The cryocatheter of claim 1, further comprising:

a first pull-wire disposed within the catheter, wherein the pull-wire has a proximal end that is slidably engaged with the second handle portion; and a second pull-wire having a distal end that is slidably engaged with the first handle portion, wherein the proximal end of the first pull-wire is engagable with the distal end of the second pull-wire.

9. The cryocatheter of claim 8, further comprising a bias element the axially biases the second pull-wire.

10. A cryocatheter system comprising:

a first handle portion having a proximal end, a distal end, a first fluid flow path, and a second fluid flow path;

a second handle portion having a proximal end, a distal end, a first fluid flow path, and a second fluid flow path, wherein the distal end of the first handle portion is matable with the proximal end of the second handle portion in fluid communication;

a flexible catheter having a proximal end, a distal end, a first fluid flow path, and a second fluid flow path, wherein the distal end of the second handle portion is matable with the proximal end of the catheter to place the respective first and second fluid flow paths of the second handle portion and the catheter in fluid communication;

a pressure sensor in communication with one of the first and second fluid flow paths, wherein the first fluid flow path is defined by a refrigerant supply tube and the second fluid flow path is defined by a fluid exhaust tube, wherein the refrigerant supply tube is in fluid communication with a vacuum source.

11. The cryocatheter of claim 10, further comprising:

a first pull-wire disposed within the catheter, wherein the pull-wire has a proximal end that is slidably engaged with the second handle portion; and a second pull-wire having a distal end that is slidably engaged with the first handle portion, wherein the proximal end of the first pull-wire is engagable with the distal end of the second pull-wire.

12. The cryocatheter of claim 11, further comprising a bias element the axially biases the second pull-wire.

13. A catheter system comprising:

a source of a fluid refrigerant, a handle having:
　a proximal handle portion coupled to said source, said proximal handle portion having first and second fluid flow pathways,
　a distal handle portion having first and second fluid flow pathways, and
　a steering element, a flexible catheter having a proximal end portion, a distal end portion, and first and second fluid flow pathways, and a coupling means for detaching and for mating the proximal handle portion from and to the distal handle portion, respectively.

14. The catheter system of claim 13, wherein the proximal handle portion is matable with the distal handle portion to place the first fluid flow pathway of the proximal handle portion in fluid communication with the first fluid flow pathway of the distal handle portion to define a first refrigerant flow pathway, and to place the second fluid flow pathway of the proximal handle portion in fluid communication with the second fluid flow pathway of the distal handle portion to define a second refrigerant flow pathway.

15. The catheter system of claim 14, wherein the first refrigerant flow pathway is in part under positive gauge pressure and the second refrigerant flow pathway is in part under negative gauge pressure.

16. The catheter system of claim 14, wherein the proximal end portion of the catheter is coupled to the distal handle portion to place the first fluid pathway of the catheter in fluid communication with the first refrigerant flow pathway, and to place the second fluid pathway of the catheter in fluid communication with the second refrigerant flow pathway.

17. The catheter system of claim 13, wherein the steering element is disposed in the proximal handle portion.

18. The catheter system of claim 13, wherein the steering element is disposed in the distal handle portion.

19. The catheter system of claim 13, wherein the steering element is configured to actuate the spatial positioning of the distal end portion of the catheter.

20. The catheter system of claim 13, wherein said coupling means is a bayonet-type connection.

* * * * *